United States Patent
Johnson et al.

(10) Patent No.: US 6,278,809 B1
(45) Date of Patent: *Aug. 21, 2001

(54) FIBER OPTIC REFLECTANCE APPARATUS FOR IN SITU CHARACTERIZATION OF THIN FILMS

(75) Inventors: Edward A. Johnson, Bedford, MA (US); Theodore F. Morse, Providence, RI (US)

(73) Assignees: Ion Optics, Inc., Waltham, MA (US); Brown University Research Foundation, Providence, RI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/086,768

(22) Filed: May 29, 1998

Related U.S. Application Data

(60) Provisional application No. 60/048,130, filed on May 30, 1997.

(51) Int. Cl.[7] .................................................. G01N 21/75
(52) U.S. Cl. ........................... 385/12; 118/688; 118/712; 250/559.27; 385/128
(58) Field of Search .............................. 385/12, 13, 128; 356/355, 357, 381, 382; 250/559.27, 559.28; 118/688–691, 712–714; 438/5, 7, 14, 16

(56) References Cited

U.S. PATENT DOCUMENTS

| | | | |
|---|---|---|---|
| 4,276,780 | 7/1981 | Patel et al. | 73/643 |
| 4,421,983 | 12/1983 | Fogle et al. | 250/339 |
| 4,668,528 | 5/1987 | Ehrlich et al. | 427/53.1 |
| 4,727,237 | * 2/1988 | Schantz | 219/121.63 |
| 4,770,895 | 9/1988 | Hartley | 427/10 |
| 4,812,650 | 3/1989 | Eckstein et al. | 250/307 |
| 4,934,313 | 6/1990 | Hartley | 118/665 |
| 5,100,233 | 3/1992 | Southwell et al. | 356/128 |
| 5,131,752 | 7/1992 | Yu et al. | 356/369 |
| 5,154,810 | 10/1992 | Kamerling et al. | 204/192.13 |
| 5,157,461 | 10/1992 | Page | 356/350 |
| 5,200,021 | 4/1993 | Kawai et al. | 156/601 |
| 5,200,023 | 4/1993 | Gifford et al. | 156/626 |
| 5,241,366 | 8/1993 | Bevis et al. | 356/382 |
| 5,313,044 | 5/1994 | Massoud et al. | 219/121.85 |
| 5,393,370 | 2/1995 | Ohta et al. | 156/626 |
| 5,399,229 | 3/1995 | Stefani et al. | 156/626 |
| 5,420,518 | 5/1995 | Schafer, Jr. | 324/653 |
| 5,425,964 | 6/1995 | Southwell et al. | 427/10 |
| 5,460,654 | 10/1995 | Kikkawa et al. | 118/726 |
| 5,536,359 | * 7/1996 | Kawada et al. | 156/626.1 |
| 5,684,574 | * 11/1997 | Shiokawa et al. | 356/382 X |
| 5,923,429 | * 7/1999 | Takeuchi et al. | 356/382 |

FOREIGN PATENT DOCUMENTS 61-288107 * 12/1986 (JP).

* cited by examiner

Primary Examiner—John D. Lee
(74) Attorney, Agent, or Firm—McDermott, Will & Emery

(57) ABSTRACT

A fiber optic reflectometer employs an optical fiber near a target substrate in a deposition chamber. The optical fiber is positioned within the chamber so that deposition of a thin film on the substrate also occurs on a portion of the optical fiber. A combination of monochromatic and broadband white light is transmitted through the optical fiber to the film deposited on it, and light reflectance measurements are made to determine, in situ and substantially in real time, such characteristics of the film as its growth rate, thickness, composition, surface roughness and refractive index. Such measurements can be made without bulk optics and without the precise alignment requirements of ellipsometry techniques and apparatus.

16 Claims, 2 Drawing Sheets

FIBER OPTIC REFLECTANCE APPARATUS FOR IN SITU CHARACTERIZATION OF THIN FILMS

RELATED APPLICATION

This application is a continuation of commonly owned and copending provisional Application No. 60/048,130 filed May 30, 1997, which is hereby incorporated by reference.

GOVERNMENT LICENSE RIGHTS

The U.S. Government has certain rights in this invention and the right in limited circumstances to require the patent owner to license others on reasonable terms, as provided for by the terms of National Science Foundation Grant number ECS9202961 and of Air Force Grant number F49620-93-1-0049.

TECHNICAL FIELD

The present invention relates to apparatus for characterizing thin films deposited on opto-electronic and photonic devices, and more particularly to apparatus for in situ monitoring, measurement and control of the optical properties of such films, without the need for bulk optics.

BACKGROUND OF THE INVENTION

Thin film deposition plays a key role in the fabrication of almost all opto-electronic or photonic devices, regardless of the means by which such films are created, such as, for example, molecular beam epitaxy (MBE), ion beam assisted deposition (IBAD), sputtering, chemical vapor deposition (CVD), or metal organic chemical vapor deposition (MOCVD).

Although the semiconductor industry represents a large market, many industrial and consumer goods also employ thin films. These include anti-reflection and scratch-resistant coatings for optics (including eyewear), the manufacture of photovoltaic cells, thermal control coatings for residential- and office-window materials, and deposition of thermal- and/or wear-resistant coatings on turbine blades, tools, and bearing surfaces. This list is hardly inclusive; the number of consumer products requiring deposition of a thin-film (or application of a thin-film coating) is estimated to be far larger than the volume of high-tech electronic and opto-electronic goods.

Whatever the application, monitoring and precisely controlling film thickness is key to maximizing the yield of high-quality, affordable parts. Accurate, real-time information on structure, quality, and film composition permits adjustment of process parameters to reliably and repeatably deliver films with the desired properties. In situ measurements now employed for certain film deposition configurations include RHEED (reflection high energy electron difraction), TOF (time of flight) ion beam surface analysis, quartz crystal monitors, and optical probe techniques, including ellipsometry and interferometry.

By far the most commonly used technique, and the only one permitting a wide-band thickness measurement, is the quartz oscillator, which performs a very indirect measurement of film thickness. Conversion from the oscillator's frequency shift to weight of the coating, then to its thickness, is prone to numerous errors arising from subtle changes in material properties (strain, density, age of crystal, temperature of sensor). Also, quartz oscillators provide no index of refraction information. Furthermore, to avoid shadowing the workpiece, crystal monitors must necessarily be placed a few inches away from the part to be coated. This results in a difference in deposition rates between the workpiece and monitor, which can fluctuate randomly from run-to-run and lead to unpredictable changes in indicated thickness.

Interferometry, ellipsometry, and other optical-probe techniques have been under development for many years and can provide a large amount of information on as-grown films. These techniques are among the most common diagnostics for post-deposition examination and evaluation of films. However, when employed as real-time diagnostics, apparatus employed in phase- and polarization-sensitive measurements must be reproducibly positioned on or about the reactor to within a fraction of a wavelength of light, not an easy adjustment to make in an industrial setting. All of these processes typically proceed "blindly," without real-time knowledge of the growing layer's characteristics. Reliable, affordable information on the structure, quality, and composition of the growing film would be welcomed and would surely lead to lower cost, swifter development of new devices, and improved quality.

Furthermore, no remote optical diagnostic can escape the need to probe the deposition region through a window; in real-life deposition systems, material is deposited not just on the substrate but also on chamber walls, fixtures, liners, and most particularly on windows. This is no small detail; windows through which interferometric or ellipsometric measurements are made must be coating-free. Although this condition can be met in a (very expensive and very slow-growing) molecular beam epitaxy (MBE) system, even with shields and shutters it is virtually impossible to achieve in the relatively high-throughput CVD reactors and physical deposition systems characteristically employed in production situations. In these systems, the environment is inherently "dirty", and it is extremely difficult to keep windows from becoming coated.

In addition to these difficulties, many important coating processes require very high temperature substrates; the growth rate and ultimate film thickness achievable by these processes can be effectively limited not by deposition conditions, but by the inability of present optical monitoring techniques to function reliably above 800° C.

SUMMARY OF THE INVENTION

According to one aspect of the invention, there is provided a system for in situ characterization of thin films deposited on a substrate. The system comprises:

a) a deposition chamber which includes an input port for introducing one or more process reactants into the chamber, an output port for exhausting by-products from the chamber, and one or more controllers for monitoring and controlling the environment within the chamber;

b) a support within the deposition chamber for supporting a substrate upon which a film is to be deposited;

c) at least one optical fiber mounted within the deposition chamber so that the film deposited on the substrate is also deposited onto at least a portion of the optical fiber;

d) a light source disposed outside of the deposition chamber and coupled to the optical fiber for transmitting light through the optical fiber to the film deposited on the fiber and establishing a light reflectance pattern from the film on the optical fiber;

e) a detector for detecting light reflected from the film on the optical fiber and for generating a signal representative of the reflected light; and f) a signal analyzer for analyzing the signal to characterize the film substantially in real time and to provide a feedback signal for controlling the environment of the chamber and the temperature of substrate to achieve desired properties of the film.

The controllers in the deposition chamber preferably control one or more of the temperature, pressure, composition and flow rate of the process reactants.

The support for the substrate preferably includes a temperature control element for controlling and regulating the temperature of the substrate before, during and after the deposition process.

The optical fiber is preferably mounted within the deposition chamber so that the film deposited on the substrate is also deposited onto an end of an optical fiber.

The light source preferably includes a source of monochromatic light and a source of polychromatic light. The two types of light are coupled into the optical fiber in a predetermined ratio. The source of monochromatic light preferably includes a light-emitting diode, such as a laser diode, and the source of polychromatic light preferably includes broadband white light.

The signal analyzer preferably includes a signal processor for smoothing the signal against fluctuations in intensity of input light. It can also include a display element for displaying the signal.

In a preferred embodiment, the optical fiber includes a plurality of deposition surfaces or end facets which are renewable or replaceable after each deposition cycle so as to present a fresh facet for deposition. The optical fiber can include, for example, a replaceable tip. In a preferred embodiment, the optical fiber is adapted for use at temperatures in excess of 1100° C. and can be made of, for example, sapphire.

The films deposited onto the substrate and the optical fiber can be formed by a deposition process selected from the group consisting of chemical vapor deposition, metal organic chemical vapor deposition, sputtering, ion beam assisted deposition, and molecular beam epitaxy. The properties of the film which can be characterized include the rate of film growth, the thickness and composition of the film, the surface roughness of the film, and its refractive index.

The process reactants can include silane and ammonia (for silicon nitride films), gallium metalorganic precursors and ammonia (for gallium nitride films), and silane and niobium chloride (for niobium silicide films.

In one embodiment, the optical fiber can be pretreated with a layer of the material of the substrate prior to deposition of a film thereon so that the surface properties of the optical fiber and the substrate are substantially the same.

According to another aspect of the invention, there is provided a method for characterizing in situ a thin film deposited on a substrate. The method comprises the steps of:
 mounting at least one optical fiber near a substrate upon which a film is to be deposited in a deposition chamber,
 transmitting light through the optical fiber to film deposited on the surface of the fiber and generating a signal representative of light reflected from the film, and
 analyzing the signal to measure growth rate, composition, thickness and refractive index of the film substantially in real time and providing a feedback signal for controlling the environment of the chamber and the temperature of substrate to control the properties of the film.

Preferably, both monochromatic and polychromatic light are transmitted through the optical fiber, wherein analysis of the reflected monochromatic and polychromatic light provides information about the film thickness, composition, refractive index and deposition rate.

Each of the following U.S. patents provide useful background for the invention, and each is hereby incorporated by reference: U.S. Pat. Nos. 5,241,366, 4,812,650, 4,668,528, 4,276,780, 5,425,964, 5,200,021, 5,100,233, 4,934,313, 4,421,983, 5,393,370, 5,154,810, 5,313,044, 5,399,229, 5,157,461, 5,200,023, 5,420,518, 5,460,654.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like elements in the FIGURES are indicated by like reference numerals.

DETAILED DESCRIPTION OF THE DRAWINGS

The invention is a fiber-optic reflectometer which can determine in situ the optical properties of thin films. The method used to make this determination closely resembles ellipsometry without the need for ultra-precise optical alignment or interrogation of the growing film through a window. According to the invention, an optical fiber is inserted into the region where material is being deposited, locating the fiber so that properties of the film grown on its tip correlate reliably with those on the substrate. In essence, this invention has turned the window-coating problem on its head; instead of confounding the measurement, concurrent deposition of the film on the optical fiber provides basis for the technique.

The invention thus includes inserting one or more optical fibers into the region where material is being deposited on a substrate, and locating the fiber or fibers so that the ends of the fibers will be coated with the material during the deposition process. If radiation from a laser diode is projected down the fiber, it will reflect both from the fiber tip and from the film that forms on the tip and that thickens on the tip as deposition proceeds. The film then becomes, in essence, a Fabry-Perot interferometer of increasing thickness, and as the back-reflected intensity varies over time (i.e, a fringing rate), it provides information on film optical thickness and growth rate. Deposition of a film on the optical fiber correlates with deposition of the film on neighboring surfaces, including the substrate.

If white light from a broad-band illumination source is projected down the fiber, it will also reflect both from the fiber tip and the film. The reflected light wavelength spectrum contains an interference pattern with information on film thickness and index of refraction at a given time.

Figure 1:
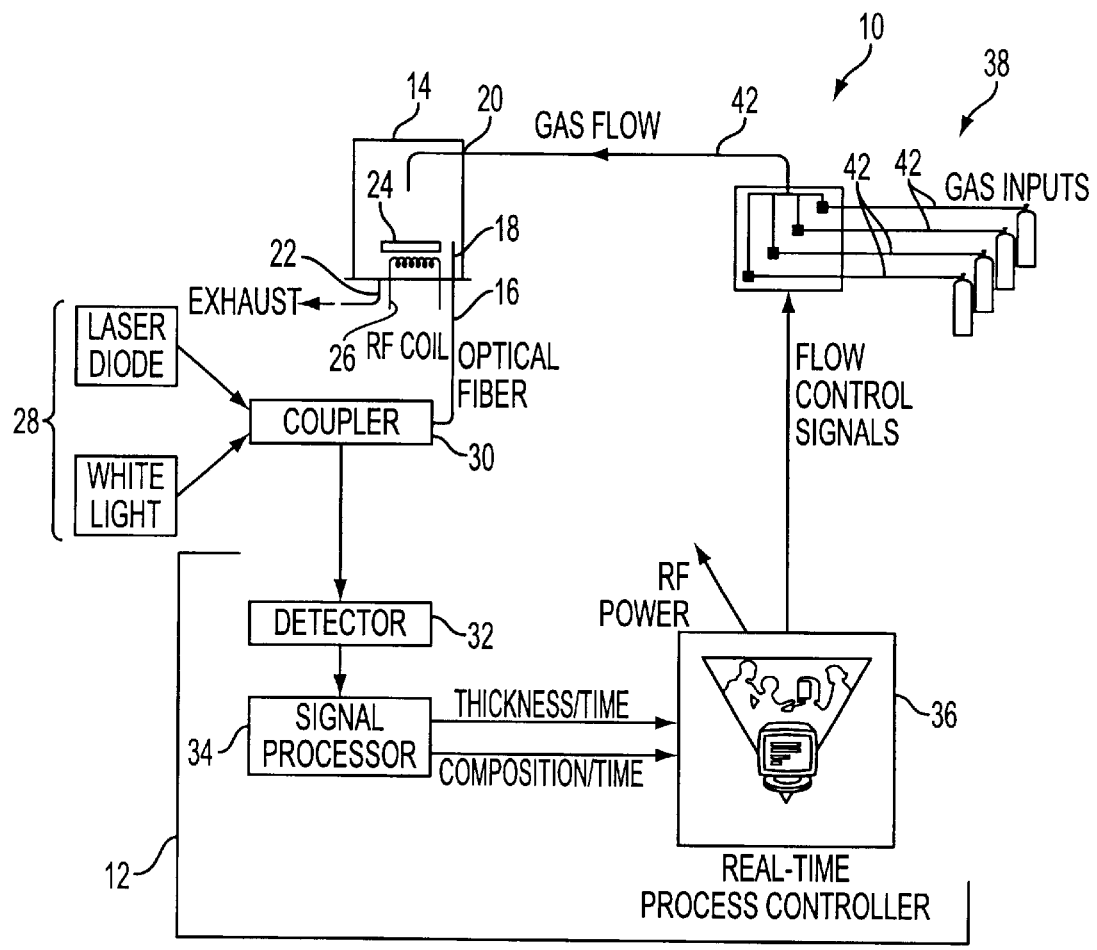
FIG. 1 is a block diagram of one system of the invention.

The reflectometer 10 of the invention is shown in block diagram in FIG. 1. It consists of two principal components: the first is a signal generation/detection unit 12 located outside the deposition chamber 14, which sends light down the fiber 16, receives the reflected signal, interprets it, and displays it. The second is a deposition unit 18 which is situated in the chamber and includes (a) a fiber tip (or tips in a multi-point system) terminating in a clean, deposit-free surface, and (b) hardware to mount and position the tip.

The deposition chamber 14 includes one or more input ports 20 for introduction of process reactants, typically in vapor form, and one or more output ports 22 for exhausting by-products of the deposition reaction. A silicon wafer 24 is disposed within the chamber and is maintained at a temperature which facilitates reaction of the process reactants and deposition of a film on the exposed wafer surface. A radio frequency coil 26 is mounted near the wafer to regulate the temperature of the wafer.

A light source 28 is provided and coupled to the optical fiber through coupler 30. The light is preferably a combination of monochromatic (single wavelength) light, such as from a light-emitting diode, and polychromatic (multiple wavelength) white light. The light is transmitted into the optical fiber 16 through the coupler 30 to the tip of the fiber onto which film is deposited. Light is reflected back into the fiber from the film to a detector 32, which generates a signal representative of the reflected light. The signal is analyzed by a signal processor 34, which provides information about the film, such as its growth rate, thickness, and composition, as well as its surface characteristics and optical characteristics, such as its refractive index. A real time process controller 36 interprets the signals from the signal processor 34 and provides feedback control signals to the reactant regulators 38 and to the radio frequency coil 26.

Figure 2:
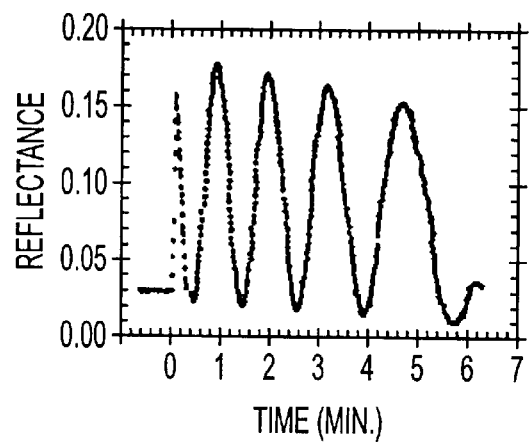
FIG. 2 is a graph illustrating light reflectance from the film as a function of time, as the film grows, in accord with the invention.
Figure 3:
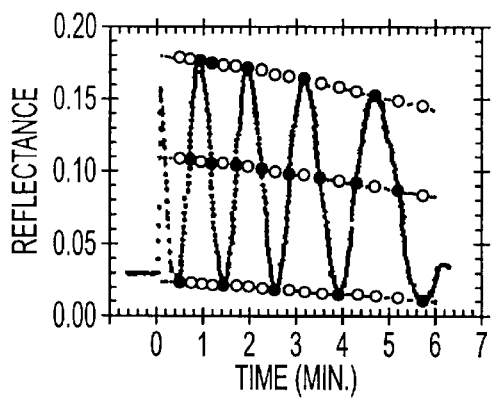
FIG. 3 is a graph illustrating maximum and minimum light reflectance, as well as surface roughness, of a film grown according to the invention.
Figure 4:
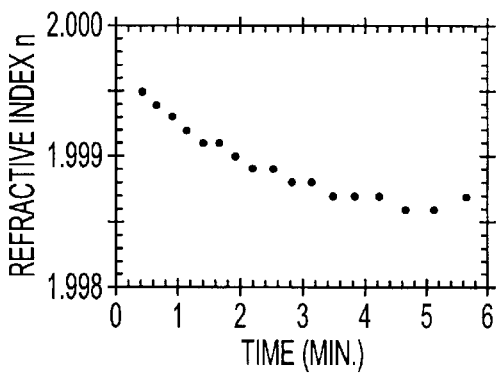
FIG. 4 is a graph illustrating refractive index of film as a function of time, as the film grows, in accord with the invention.
Figure 5:
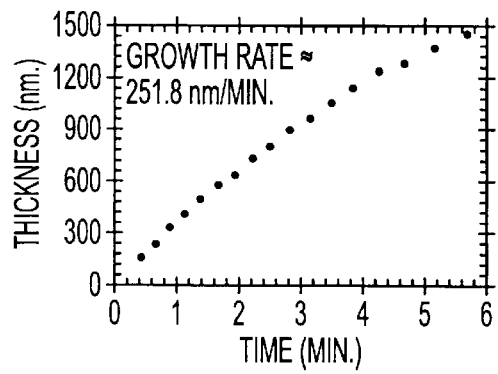
FIG. 5 is a graph illustrating film growth rate (thickness as a function of time)
Figure 6:
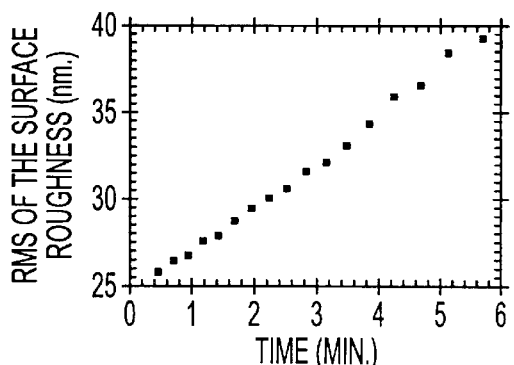
FIG. 6 is a graph illustrating surface roughness of film as a function of time.

FIGS. 3–6 illustrate information which can be obtained with the fiber optic reflectometer of the invention. FIG. 2 illustrates reflectance of the light from the film on the optical fiber as a function of time, i.e., as the film is being deposited on the fiber and on the substrate. The reflectance signal oscillates between minima and maxima, as indicated more clearly in the graph of FIG. 3, and generally decreases slightly with time and increasing thickness of the film. FIG. 4 illustrates the refractive index n of the film as a function of deposition time, and therefore of film thickness, and this value also is seen to decrease with increasing film thickness. FIG. 5 illustrates the film growth rate, i.e., film thickness as a substantially linear function of deposition time. FIG. 6 illustrates surface roughness as a substantially linear function of deposition time. All of this information is provided by the light reflected from the film deposited on the exposed end of the optical fiber, as detailed more fully below.

Figure 7A:
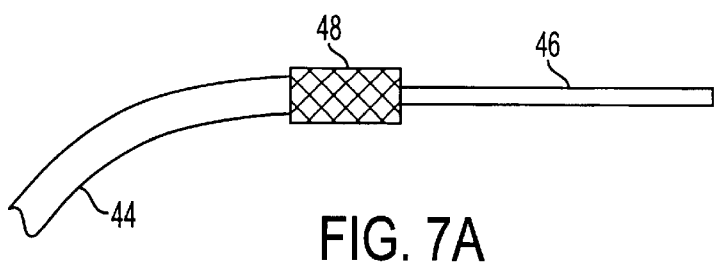
FIG. 7A is a simplified diagram of one embodiment of an optical fiber having a replaceable or renewable tip.
Figure 7B:
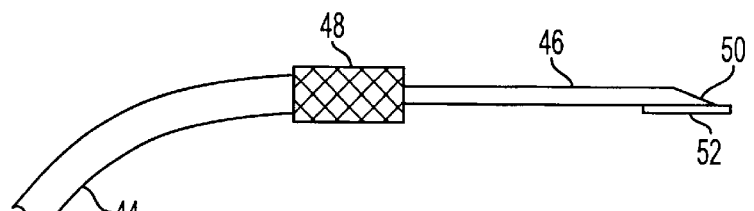
FIG. 7B is a simplified diagram of another embodiment of an optical fiber having a replaceable window at the tip.

For the fiber optic reflectometer of the invention to be useful in an industrial environment, it is preferable that a clean deposition surface be provided after every run, or after a number of runs which can be empirically determined. To obtain this surface, the fiber is cleaved at its tip, or it is fit with a replaceable or refurbishable tip. Alternative configurations for the tip are illustrated in FIGS. 7A and 7B. In FIG. 7A, the optical fiber bundle 44 is coupled to a replaceable tip 46 via a connector 48. Both ends of the tip 46 are polished, and the tip is placed in the plane of the substrate (not shown). After the deposition cycle has completed, the tip 46 is removed from the bundle, repolished, and/or replaced.

Commercially available fiber tips are simple light pipes (or rods), typically 1-inch long, with polished end facets. They connect quickly and easily to the fiber through a standard fiber-optic connector into which the rod is glued, greatly simplifying tip replacement. Manufacturing methods used to fabricate the light-pipe tips result in highly reproducible alignment with the fiber bundle.

In FIG. 7B, another configuration is shown. The tip 46 has a beveled mirrored face 50 and a replaceable, relatively inexpensive window 52 over the deposition facet. This configuration is useful in rotary stage deposition. The window instead of the tip is removeable and replaceable after one or more deposition cycles. For side deposition, which is required to locate fiber tips over rotary stages, either a bend is made in the light pipe, or the right angle facet and side window are polished directly into the end of the light pipe.

The optical fiber is preferably positioned within the chamber to permit reproducible adjustment of the fiber in three dimensions, to avoid shadowing the substrate, to avoid interference with other operations or mechanisms, to be vacuum compatible, to provide an indication when the fiber is correctly positioned, to be simple and easy to use, and to be adaptable to a variety of deposition systems.

In a high-temperature system, the difficulty of meeting these requirements is compounded by the effects of thermal expansion. Fiber tips should be precisely and reproducibly located within very tight tolerances to assure run-to-run repeatability of measurements.

For maximum rigidity, mounting hardware should be supported from a point as close to the sample as possible; variations in reactor design (vertical versus horizontal sample, stationary versus rotating, top-loaded versus bottom- or side-loaded, cold-wall versus hot-wall, etc.), make it difficult to achieve a high degree of universality in a close-mounted design. An alternative is to support a mount of stock design from an adjustable arm carried on a standard vacuum flange installed on a chamber port.

The energy source for the deposition chamber can be, for example, a Lepel 2.5 kW power supply which, through induction coils, heats a carbon susceptor to the desired temperature. Temperature measurements in induction heated reactors typically employ emissive techniques, however, in this method radiation emitted from interior walls changes its character as the wall of the reactor becomes coated. The emissivity of not only the carbon, but also of the deposited material affects the temperature reading. For this reason, a high-temperature thermocouple probe, rather than pyrometric methods, can be used. The thermocouple can be located at a point where it does not interrupt flow dynamics on the substrate, but does indicate a temperature representative of the substrate surface. Since the thermocouple itself has a very small cross section, it does not disturb the e-field significantly. To make a measurement with the thermocouple, the power supply must be turned off. During this off interval, a temperature measurement is made and used for feedback control of reactor temperature.

Silicide films are, in general, somewhat metallic. Thus, they will not be highly transparent at either visible or IR wavelengths. Nevertheless, a metallic film is transparent if sufficiently thin.

In addition to its usefulness as a thin-film growth diagnostic, the apparatus and methods of the invention can also be applied to monitor the deposition of ¼ wave stacks of layers with alternating refractive index, used to produce mirrors for optical components. This task is performed with interferometric methods and bulk optics, if the sample is large enough; prior to the invention, however, real-time changes in the reflectivity of diode laser mirrors grown after the laser wafers have been diced cannot be monitored in this way. This limitation is overcome by inserting an optical fiber into the deposition region, as described in connection with the invention. The thin layers growing on the end of the fiber then mimic growth on the laser facets, and their properties can be deduced from interference patterns, as described herein.

It should be noted that for process monitoring and feedback control applications, it is not necessary, or even important, that the films deposited onto the fiber optic tip and onto the substrate wafer should be identical to each other. It is sufficient that the properties of both films are related to each other and to the deposition conditions in a deterministic and reproducible way. Deposition on the substrate and on the optical fiber may not necessarily proceed at the same rate as on the substrate. If it does not, the end of the fiber can be pre-coated or otherwise pretreated with an ultra-thin layer of substrate material prior to deposition so that the surface kinetics of the respective elements are similar, and film growth initiates and proceeds in identical ways on both the fiber and the substrate wafer.

A significant advantage of fiber optic reflectance measurements with incoherent light is that this technique allows straightforward time-multiplexing of various signals without regard to polarization, alignment, or wafer and optical fiber orientation. This not only simplifies measurements on rotary or planetary wafer fixtures (common in CVD reactors), but it also allows phase-locked detection for immunity from background illumination in the deposition region.

In addition, this technique permits simultaneous laser interferometry and white-light spectral reflectance measurements. The information from these two measurements is quite complementary. As described herein, pulsed laser interferometry allows measurement of a "fringing rate" which, to first order, reveals the instaneous film deposition rate. At the same time, white-light spectral reflectance measurements provide information about the overall film composition and structure. In theory, the structure of the total film is simply the time integral of all of the instantaneous film measurements. However, in practice, deposition occurs at an elevated temperature, and diffusion within the previously deposited layers occurs even as new layers are being deposited. For many optoelectronic device structures this dynamic diffusion is a critical determinant of the final device structure.

Information contained in these measurements will yield film thickness as a function of time, refractive index as a function of time (or length), and mean surface roughness, as previously described in connection with FIGS. 4–6. All of this information is obtained simply by inserting an optical fiber into the reaction chamber through an appropriate bulkhead mount. No additional optics are required, and there is no need for the extremely precise alignment demanded by ellipsometry. An additional advantage is its immunity to electrical noise generated by the plasmas and rf fields which are a feature of many deposition reactors.

There is no general closed-form solution for the reflectivity of a material with an index of refraction which varies as a function of film depth. Because of this, the procedure is computed to fit to measured data by assuming that the implanted region of the wafer is composed of a number of thin slabs and assuming that each slab has the index of refraction and absorption characteristics of the wafer at that depth. Since film thickness and index of refraction data are backed out of the measured optical data by a process of successive approximation, the quality and the performance time of this simulation depend on the number of layers used to approximate the actual profile of the wafer.

One method of calculating indices of refraction for transitional regions employs an effective media approximation (EMA) that recasts the optical transfer matrix equations to reduce the number of required parameters and change the evaluations from transcendental functions to exponentials. This simple but powerful technique for performing global fit optimization removes the requirement for accurate starting guesses and allows the program to run effectively without operator intervention.

There are several advantages to the use of an optical fiber in materials-processing diagnostics. The fiber can be easily adapted to relatively high temperatures and high-vacuum systems, and, by utilizing back-reflection from the fiber end, inconveniences associated with the alignment required for traditional bulk optical systems are avoided. Further, because of the small cross section of the fiber, spatial resolution can be quite high. By injecting pulsed light and employing digital signal processing techniques, the back-reflected light can be readily distinguished from infrared radiation present in a high temperature environment. This significantly increases the signal/noise ratio. In our optical measurement of thin-film growth, we measure the ratio of incident to back-reflected intensity. With this ratio, the method described below yields the film's optical constants from the measured positions of interference maxima and minima and the points of zero interference.

The measurement consists of several steps. First, the optical fiber is inserted into a deposition chamber near a substrate on which deposition is to be measured. As the film is deposited on the substrate and on the end of the optical fiber, which starts as a pristine, flat quartz surface, a Fabry-Perot interferometer forms at the fiber tip. Oscillations in the intensity of back-reflected light provide immediate information on the film growth vs. time curve. Used in conjunction with these measurements, a self-consistent calculation can be made to obtain film parameters. The model used is a Fabry-Perot interferometer with a moving interface, in which the refractive index of the film and the surface roughness appear as parameters. A closed system of equations developed from experimental values can be solved simultaneously for these parameters as a function of film thickness.

The method is based on the use of the Airy's reflectance formula, presented in most optics textbooks in sections on plane plate or film interference phenomena. The formula requires as inputs the values of the forward (i.e., into the film) and backward reflection coefficients (coded R and S, respectively) and also a product of the forward and backward transmission coefficients (coded T) of the transitional regions of the film. These quantities, although complex and oscillatory, can be converted into smooth monotonic functions by changing them from real and imaginary to magnitude and phase representations, respectively (in fact, only R and T require such changes). The phases have to be treated further to make sure that they are continuous, since initially they are computed in the range between −π and π, although the actual phase is usually monotonically decreasing indefinitely. Instead of eight (real) oscillating functions, this produces only six such functions which are smooth enough for quick linear interpolation.

To compute the resultant reflectance for a given wavelength, it is most convenient and computationally advantageous to repeatedly apply an optimized variant of the Airy's reflectance formula, starting with the surface region, and continuing with the rest of the "flat" layers, in the direction opposite to that of incidence. To apply the formula to the deposition region, it is required to know the R, S and T coefficients for the front transition region and the S coefficient for the back transition region. For the sharp interfaces between the "flat" regions, the code computes R, S, and T from their complex refractive indices The back surface internal reflection coefficient for later layers is precomputed by the Airy's formula.

To obtain accurate film thickness, it has heretofore been necessary to know the refractive index of the film material. For a sufficiently well-defined range of material compositions, this can be obtained by modeling the optical behavior of the deposition process, as described below. A series of iterations is performed until a self-consistent calculation giving values of film thickness, refractive index, and surface roughness which causes the model to agree with experiment is obtained. In practice, a challenge of the program will be to optimize the interaction between the diode laser and white light measurements, using shared optical constants, computed in real time.

In order to achieve these goals, both white light and monochromatic light from a laser diode are transmitted into the fiber. The growth of the film can be measured using the laser diode. It is possible to make real time measurements of reflection characteristics using a spectral detector array. This instrument takes several seconds to acquire a spectral scan so the growth will be stopped and the gas stream vented to avoid the problem of additional growth during the monochromator scan.

Stacks of varying composition can be examined by measuring the optical reflectance as a function of changing reactant flow rate. This will enable the user, through the changing refractive index, to examine the effects of compositional diffusion during the deposition process. In addition, the effects of diffusion during layer growth can be observed by maintaining a film model based on deposition rate updates from the diode laser measurements and comparing this model to the model obtained from periodic white light updates. Experimental measurements of reflectance (R)-vs.-time are readily converted to thickness (1)-vs.-time using the following procedure.

(1) the data is smoothed by averaging over 1000 samples (at a sampling rate of 4,000 Hz). From this smoothed function we obtain the first and second derivatives, R'(t) and R"(t), respectively;

(2) the locations and values of the maxima (R"(t)<0), the minima (R"(t)>0), and the inflection points where R"(t)=0 are obtained;

(3) Curves are fit through the maxima, minima, and inflection points to yield $R_{max}$, $R_{min}$, and $R_S$ as functions of position (or time). This procedure was used to calculate the curves for $R_{max}$, $R_{min}$, and $R_S$.

Thus, at each position there are three equations (one for each of the unknowns) to be solved numerically.

Applications which will benefit from the invention include the growth of etch masks and dielectric isolation and extend beyond electronics to the production of anti-reflection and scratch-resistant coatings for optics (including eyewear), to the manufacture of photovoltaic cells, and to deposition of thermal- or wear-resistant coatings on turbine blades, tools, and bearing surfaces. In many of these applications, precise thickness control is not critical; in others, quartz crystal deposition gauges are employed to track film growth. The initial cost of a quartz crystal system is about ten thousand dollars; it is estimated that five to ten thousand such systems are now being sold annually in the United States, representing a hundred million dollar market (not including service and spares). A commercially significant number of these systems (those used to monitor coatings transparent in the visible and infrared, of which the silicon nitride is an important example) could be replaced by the easy-to-use fiber-optic reflectometers described herein and selling for a few thousand dollars each, saving industry tens of millions of dollars a year.

Thus, by examining the interferometric fringes in back-reflected light from an optical fiber placed in a CVD reactor, a simple technique for in situ measurement of film growth is provided. A model which assumes an increasing Fabry-Perot cavity and uses the experimental data as input can be used to solve numerically for the refractive index, film thickness, and surface roughness as functions of position or time. Thus, a priori knowledge of the refractive index is not necessary to obtain growth rates from the data. Since no bulk optics are needed for the measurement, the technique is easy to apply.

EXAMPLE

In these experiments, a multimode optical fiber with a 100 mm core and 140 mm cladding was used. This large core insured sufficient back-reflected signal. The fiber carried light into the reaction region, where deposition occurred on the end of the fiber, and it also transmitted back-reflected light from the deposited film. The light source was an 850 nm laser diode (other convenient diode laser wavelengths are 1300 and 1550 nm; these could be used for materials whose wavelength cut-off is below 1000 nm).

Incoherent white light was provided by an Ocean Optics LS-1 tungsten-halogen lamp, injected into a fiber and transmitted through a Canstar 2×2 fiber optic coupler to the deposition chamber. One of the fibers on the chamber side of the coupler was not needed to carry signals to-and-from the deposition chamber and was therefore immersed in an index matching fluid to quench optical noise reflected from its face. The second fiber passed through the chamber wall and was mounted near the substrate. The protective plastic sheath encasing the fiber's core and cladding was removed prior to its insertion into the chamber to eliminate the potential for outgassing. Reflected signals were transmitted back through the 2×2 coupler to an Ocean Optics SD-2000 Spectrometer. Data acquired by the spectrometer was passed to a digital computer through a D/A board supplied by the spectrometer manufacturer, and there it was analyzed by Ocean Optics' software. Before every deposition run, the fiber tip was removed from its mount and cleaved to insure a pristine surface.

Since variation in the back-reflected signal can be quite small, fluctuations in laser intensity were expected to degrade the experimental results. Several signal processing methods were used to improve the signal/noise ratio. The laser was pulsed at 270 Hz, and for each point on the curve, 1024 data points were taken at 4000 points/sec. This information was processed using a fast Fourier transform. At zero Hz, the signal increases with temperature. The inverse Fourier transform was then taken from data monitored at 270 Hz, and these data were fit with polynomials. It is the time multiplexing inherent in the use of a pulsed laser which permits the user of the fiber optic reflectometer to obtain accurate data at high temperatures.

For a fiber optic waveguide in which light propagates through the fiber by total internal reflection (Eq. 1), when light reaches the fiber tip, the difference in index of refraction between the fiber core (n=1.458) and air or vacuum (n=1) causes, according to the formula for normal Fresnel reflection, about 4% to be reflected back into the fiber at the freshly cleaved tip:

$$R = \frac{(n-1)^2}{(n+1)^2} \qquad (1)$$

The index of the fiber is generally a function of wavelength $\lambda$, however, in the spectral region produced by a white light source (400 nm to 850 nm), dispersion resulting from this wavelength dependence can be neglected because it is quite small. As a thin film of index $n_1$ is deposited on the fiber tip, total reflection along the fiber is modified by interference with light from the glass-film and film-vacuum interfaces. These effects are particularly pronounced when the following condition relating film thickness and light wavelength is met:

$$n_1(\lambda)d = N\frac{\lambda}{4} \qquad (2)$$

where $n(\lambda)$ is the index at wavelength $\lambda$, d is film thickness, and N is a positive integer. If N is even, the coating is said to be neutral and reflection is that of the bare fiber/vacuum interface; if N is odd, reflection will be either maximized (if the film index is higher than the substrate index) or minimized (if the converse is true).

There are two ways to measure these interference effects. At a fixed wavelength, the growing film causes reflectance to pass through periodic maxima and minima, between the value corresponding to the bare substrate and a second value, either greater or smaller, depending on the indices. Alternatively, a spectral snapshot can be taken at a given thickness, and peaks and valleys in the reflectance observed for those wavelengths where condition (2) is met.

The complete expression for the reflectance of a single layer on a substrate is quite complex $$R = \frac{(n_0^2 + n_1^2)(n_1^2 + n_2^2) - 4n_0 n_1^2 n_2 + (n_0^2 - n_1^2)(n_1^2 - n_2^2)\cos(2\delta)}{(n_0^2 + n_1^2)(n_1^2 + n_2^2) + 4n_0 n_1^2 n_2 + (n_0^2 - n_1^2)(n_1^2 - n_2^2)\cos(2\delta)} \qquad (3)$$

where $n_0$, $n_1$ and $n_2$ are the (wavelength dependent) fiber core (substrate), film and air indices respectively, and $\delta = 2\pi n_1 d/\lambda$. It is assumed that all layers are transparent. For this and more complex situations, it is usually preferable to have access to an optical thin-film simulation package. For the NSF/STTR program, FilmStar, by FTG Associates, was employed to model reflectance spectra.

For the alumina films, the refractive index is very close to 1.6 in the visible region of the spectrum. With an index value for the fiber core of 1.458, the following expression is obtained:

$$R = \frac{1.75 - 0.68\cos(2\delta)}{31.43 - 0.70\cos(2\delta)} \approx 0.0557 - 0.0216\cos(2\delta) \qquad (4)$$

Thus, reflectance is expected to have a sinusoidal dependence on wavelength. More rapid interference cycles are observed at shorter wavelengths, where higher measurement precision is obtained. A single-wavelength source allows for a very powerful signal, but introduces noise associated problems.

Such problems arose when strong in-band light emission from the evaporator's crucible as coupled into the fiber and interfered with measurement of the reflected signal. Background amplitude was high in the visible region, a particularly important consideration given that reflection was only 4-to-8% for the fiber and coating indices involved. However, if a broad spectral source (white light) is used in conjunction with a spectrometer employing a solid-state detector array, it is possible to obtain reflectance spectra in real time. In the output from this device, positions of the maxima correspond to odd multiples of $\lambda/4n_1$, and can be used to determine film thickness directly, minimizing the impact of optical noise on the monitoring process.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. A system for in situ characterization of thin films deposited on a substrate, comprising:
   a) a deposition chamber, including input means for introducing one or more process reactants into the chamber, output means for exhausting by-products from the chamber, and means for monitoring and controlling the environment within the chamber;
   b) means within the deposition chamber for supporting a substrate onto which a film is to be deposited;
   c) one or more optical fibers mounted within the deposition chamber so that the film deposited on the substrate is also deposited onto at least a portion of an optical fiber;
   d) a light source disposed outside of the deposition chamber and coupled to the optical fiber for transmitting light through the optical fiber to the film deposited on the fiber and establishing a light reflectance pattern from the film on the optical fiber, wherein the light source comprises a source of monochromatic light and a source of polychromatic light and means for transmitting both types of light through the optical fiber;
   e) detector means for detecting light reflected from the film on the optical fiber and for generating a signal representative of the reflected light; and
   f) means for analyzing the signal to characterize the film substantially in real time and to provide a feedback signal for controlling the environment of the chamber and the temperature of the substrate to achieve desired properties of the film.

2. A system according to claim 1, wherein the means for monitoring and controlling the environment within the chamber includes means for controlling one or more of the temperature, pressure, composition and flow rate of the process reactants.

3. A system according to claim 1, wherein the means for supporting a substrate includes means for controlling the temperature of the substrate.

4. A system according to claim 1, wherein the optical fibers are mounted within the deposition chamber so that the film deposited on the substrate is also deposited onto an end of each optical fiber.

5. A system according to claim 1, wherein the optical fiber is pretreated with a layer of the material of the substrate prior to deposition of a film thereon so that the surface properties of the optical fiber and the substrate are substantially the same.

6. A system according to claim 1, wherein the source of monochromatic light comprises a light-emitting diode and the source of polychromatic light comprises white light.

7. A system according to claim 1, wherein the means for analyzing the signal comprises signal processing means for smoothing the signal against fluctuations in intensity of input light, and means for displaying the signal.

8. A system according to claim 1, wherein the optical fiber includes a plurality of deposition surfaces.

9. A system according to claim 8, further comprising means for providing a renewable deposition surface on each optical fiber.

10. A system according to claim 9, wherein the optical fiber includes a replaceable tip.

11. A system according to claim 10, wherein the optical fiber includes a cleaved end facet for deposition of the film thereon.

12. A system according to claim 1, wherein the optical fiber is adapted for use at temperatures in excess of 1100° C.

13. A system according to claim 1, wherein thin films are formed by a deposition process selected from the group consisting of chemical vapor deposition, metal organic chemical vapor deposition, sputtering, ion beam assisted deposition, and molecular beam epitaxy.

14. A system according to claim 1, wherein the properties of the film which can be characterized are selected from the group consisting of the rate of film growth, film thickness, film composition, film surface roughness and film refractive index.

15. A system according to claim 1, wherein the process reactants are selected from the group consisting of silane, ammonia, gallium metalorganics, niobium chloride, metalorganics, and silicon precursors, and wherein the film is selected from the group consisting of silicon, quartz, gallium arsenide, sapphire, silicon nitride, gallium nitride, and niobium silicide.

16. A method for characterizing in situ a thin film deposited on a substrate, comprising the steps of:

mounting an optical fiber near a substrate onto which a film is to be deposited in a deposition chamber, transmitting light through the optical fiber to the film deposited on the surface of the fiber and generating a signal representative of a reflectance pattern of light from the film, wherein both monochromatic and polychromatic light are transmitted through the optical fiber, and wherein analysis of the reflected monochromatic and polychromatic light provides information about the film thickness, composition refractive index and deposition rate, and analyzing the signal to characterize the film substantially in real time and provide a feedback signal for controlling the environment of the chamber and the temperature of the substrate to achieve one or more desired properties of the film.

\* \* \* \* \*